United States Patent [19]
Zehrung

[11] Patent Number: 5,651,143
[45] Date of Patent: Jul. 29, 1997

[54] ARM SLING

[76] Inventor: Raymond E. Zehrung, 3029 Cameron Way, Santa Clara, Calif. 95051

[21] Appl. No.: 504,018

[22] Filed: Jul. 19, 1995

[51] Int. Cl.$^6$ .................. A61F 5/40; A47D 13/02
[52] U.S. Cl. .................. 2/338; 2/16; 2/321; 224/159; 602/4
[58] Field of Search .................. 602/4, 5, 20, 21; 224/159, 158, 160, 257, 258, 260, 150, 578, 579, 901.4, 15; 2/16, 104, 338; 128/877, 878, 876

[56] References Cited

U.S. PATENT DOCUMENTS

| | | | |
|---|---|---|---|
| 522,018 | 6/1894 | Kehlenbeck | 224/159 |
| 554,019 | 2/1896 | Collins | 224/159 |
| 1,266,688 | 5/1918 | Kassner . | |
| 1,490,066 | 4/1924 | Car | 224/579 |
| 1,490,381 | 4/1924 | Gobar | 602/4 |
| 1,760,443 | 5/1930 | Scheidegger | 224/159 |
| 2,543,847 | 3/1951 | Hallstedt | 604/4 |
| 2,607,340 | 8/1952 | Anderson | 602/4 |
| 2,812,123 | 11/1957 | Girton | 224/578 |
| 3,275,205 | 9/1966 | Howd et al. | 224/578 |
| 3,295,501 | 1/1967 | Riley | 2/338 |
| 3,297,026 | 1/1967 | Van Pelt | 128/878 |
| 3,404,680 | 10/1968 | Gutman et al. | 128/94 |
| 3,554,194 | 1/1971 | Johnson | 128/94 |
| 3,706,310 | 12/1972 | Garnett | 602/4 |
| 3,841,542 | 10/1974 | Hogensen, Jr. | 2/338 |
| 4,327,850 | 5/1982 | Robinson, Jr. | 224/579 |
| 4,355,635 | 10/1982 | Bihl et al. | 602/4 |
| 4,436,233 | 3/1984 | Hill et al. | 224/159 |
| 4,446,858 | 5/1984 | Verter | 602/4 |
| 4,651,349 | 3/1987 | Heiler | 2/104 |
| 4,716,895 | 1/1988 | Marques et al. | 128/94 |
| 4,733,685 | 3/1988 | Ruthven, Jr. | 128/94 |
| 4,751,923 | 6/1988 | Marino | 602/4 |
| 4,759,353 | 7/1988 | Melendez et al. | 602/4 |
| 4,815,639 | 3/1989 | Lehman | 224/159 |
| 5,081,714 | 1/1992 | Liu | 2/338 |
| 5,141,488 | 8/1992 | Schrader | 602/4 |
| 5,165,584 | 11/1992 | Meagher et al. | 224/258 |
| 5,188,587 | 2/1993 | McGuire et al. | 602/20 |
| 5,353,538 | 10/1994 | Hakedal et al. | 42/85 |
| 5,358,470 | 10/1994 | Johnson | 602/20 |
| 5,458,267 | 10/1995 | Curtis et al. | 2/338 |
| 5,460,308 | 10/1995 | Hahn | 224/258 |

FOREIGN PATENT DOCUMENTS

| | | | |
|---|---|---|---|
| 2674114 | 9/1992 | France | 224/159 |
| 603153 | 8/1978 | Switzerland | 602/4 |
| 1560260 | 1/1980 | United Kingdom | 224/159 |

*Primary Examiner*—Amy B. Vanatta
*Attorney, Agent, or Firm*—David R. Gildea

[57] ABSTRACT

An arm sling for supporting an arm holding a baby. The arm sling includes a shoulder loop and an arm strap extending from the shoulder loop. The end of the arm strap is detachably fastened to the front of the shoulder loop with Velcro to make an arm support loop having an adjustable length for supporting the arm holding the baby. When not in use, the arm sling may be folded and squeezed into a compact bundle and stowed in a pants pocket.

9 Claims, 1 Drawing Sheet

ARM SLING

BACKGROUND OF THE INVENTION

1. Field of the Invention

The invention relates generally to arm slings and more particularly to an adjustable sling for supporting an arm that holds a baby.

2. Description of the Prior Art

Slings and pouches have been used for many years for holding and carrying babies. One familiar type of sling comprises a triangular or rectangular cloth which is secured behind or on one side of the neck of a wearer by knotting or otherwise attaching the corners. The sling either descends directly or crosses the from of the wearer. The baby is held and enclosed in a pouch that is formed by opening the cloth. Such slings have the advantage of being inexpensive but are cumbersome to use and adjust and can be uncomfortable due to pressure on or across the neck of the wearer. A further difficulty is that a large surface area of cloth is required, thereby making the sling difficult to carry about when not being used.

Various pouches are commercially available for holding and carrying babies on either the back or the front of the wearer. A backpack type of pouch has the advantage of being able to support a larger and/or heavier baby with relatively less strain to the wearer. However, some babies, especially younger ones, are unhappy and become fussy unless held facing the front of the wearer. Further, existing commercial pouches of both back and front types are relatively expensive, difficult to carry when not in use, and cannot easily be adjusted without taking the baby out of the pouch and the pouch off of the wearer.

Some babies need to be held but become frustrated and cry when not free to move their upper bodies about. Existing commercial pouches do not work for these babies because the pouches overly restrict the baby's movement. Yet, holding the baby can quickly become tiring for the holder, especially if the holder needs to hold the baby in only one arm in order to have the other arm free.

SUMMARY OF THE INVENTION

It is therefore an object of the present invention to provide an arm sling for supporting an arm for holding a baby.

Another object is to provide an arm sling for holding a baby facing against the front of a wearer.

Another object is to provide an arm sling that allows a baby freedom to move his/her upper body while being held.

Another object is to provide an arm sling that is supported on a shoulder of a wearer.

Another object is to provide an arm sling that stows in a pocket when not in use.

Another object is to provide an arm sling that is inexpensive.

Another object is to provide an arm sling that is easy to use.

Another object is to provide an arm sling that is adjustable in length.

Briefly, in a preferred embodiment, the arm sling includes a shoulder loop and an arm strap extending from the shoulder loop. The shoulder loop is supported on a shoulder of a wearer. The end of the arm strap is detachably fastened to the front of the shoulder loop with a flexible, pressure sensitive fastening strip such as VELCRO to make an arm support loop for supporting the arm extending from the opposite shoulder for holding a baby.

An advantage of the present invention is that the arm sling reduces arm fatigue by supporting the arm that is holding the baby.

Another advantage of the arm sling is that the baby is less fussy because he/she is held facing the front of the wearer.

Another advantage of the arm sling is that a baby does not become frustrated by not being able to move his/her upper body.

Another advantage is that the arm sling is more comfortable by being supported on a shoulder and not on the neck of the wearer.

Another advantage is that the arm sling stows in a pocket when not in use.

Another advantage is that the arm sling may be inexpensively made of a single length of cloth material.

Another advantage is that the arm sling is easy to use by leaving one arm and hand free and having only a single, easily detachable fastening that may be adjusted by the free hand.

Another advantage is that the arm sling uses the fastening to adjust the length of the arm support loop to the various sizes of wearers.

These and other objects and advantages of the present invention will no doubt become obvious to those of ordinary skill in the art after having read the following detailed description of the preferred embodiments which are illustrated in the various figures.

IN THE DRAWINGS

DETAILED DESCRIPTION OF THE PREFERRED EMBODIMENTS

Figure 1:
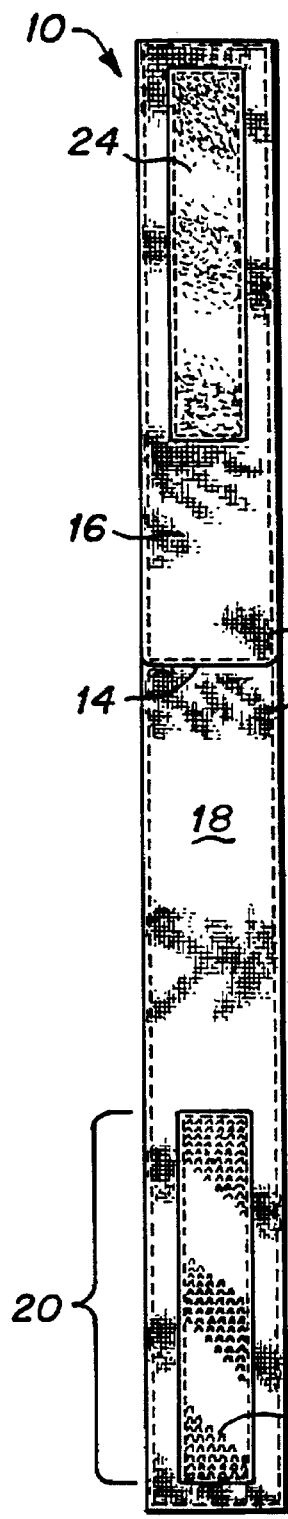
FIG. 1 is a front view of the present invention of an arm sling.
Figure 2:
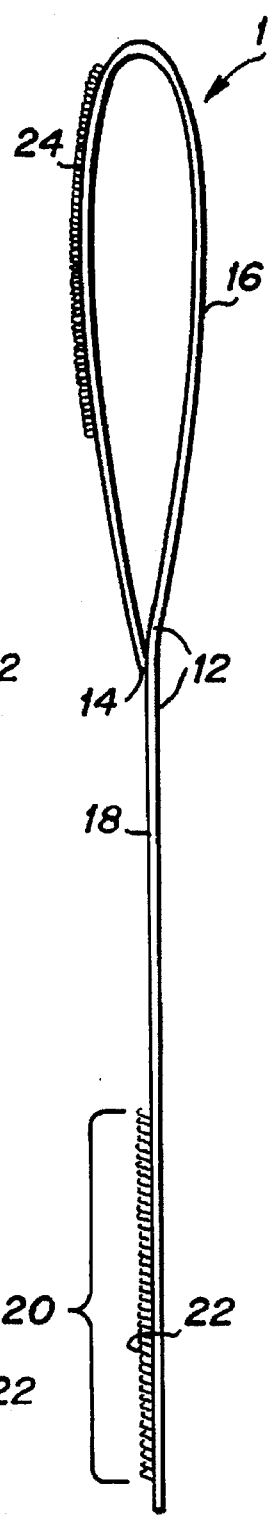
FIG. 2 is a side view of the arm sling of FIG. 1.

FIGS. 1 and 2 illustrate a front view and a side view, respectively, of an arm sling of the present invention referred to herein by the general reference number 10. The arm sling 10 is made of a continuous length of flexible material 12. The material is attached to itself at a mid-line 14 to form a shoulder loop 16. The shoulder loop 16 has a longitudinal direction passing through the midpoint 14 in a plane formed by the loop of the shoulder loop 16. An arm strap 18 extends in the longitudinal direction from the mid-line 14 to a strap end section 20. The front side of the strap end section 20 includes a first fastening 22. The outward facing front side of the shoulder loop 16 includes a second fastening 24.

The material 12 is approximately four to ten centimeters wide and one hundred thirty to one hundred seventy centimeters long. In a preferred embodiment, the material 12 is padded, quilting cloth that is folded over so that the finished side of the cloth shows on both sides of the flexible material 12. The cloth is then folded inwardly along the edges and sown to give an overall finished appearance. The mid-line 14 is positioned to give the shoulder loop 16 a length about the loop of approximately sixty to one hundred centimeters. The first fastening 22 is a flexible, pressure sensitive detachable fastening strip made of a material such as VELCRO material approximately three to ten centimeters wide and approximately fifteen to thirty centimeters long. The second fastening 24 is a second flexible, pressure sensitive strip such as VELCRO to mate with the first strip also approximately three to ten centimeters wide and approximately fifteen to thirty centimeters long. Of course, various other well-known fastenings can be used for the first and second fastening 22 and 24 including straight pins, safety pins, mating snap fasteners, buttons and button holes, hooks and hook retainers, a buckle and buckle holes, a lace and lacing holes, a zipper, or a combination of any of the above. Or the first and second fastenings 22 and 24 can be permanently attached.

Figure 3:
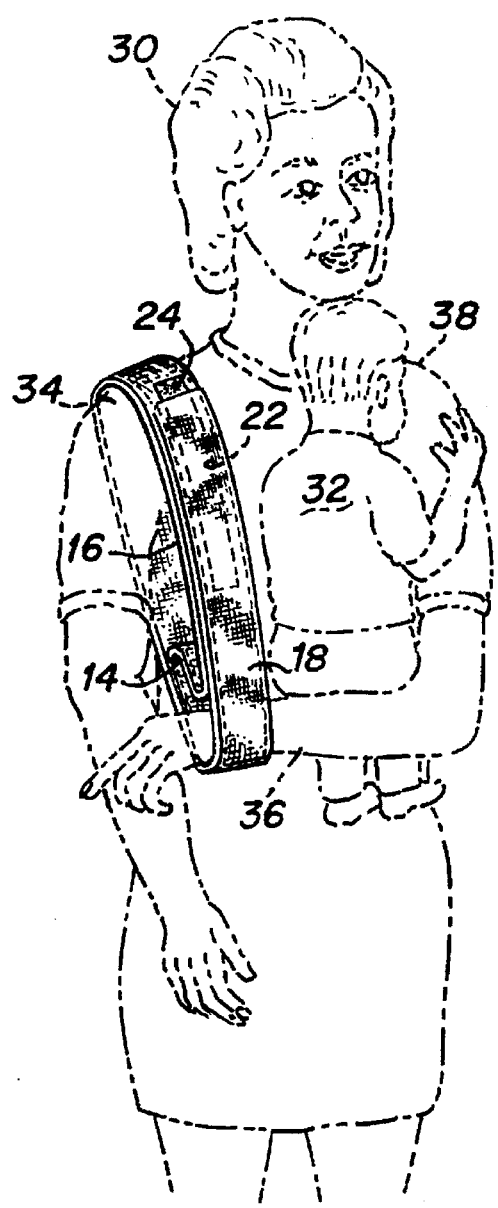
FIG. 3 is a drawing of a wearer using the arm sling of FIGS. 1 and 2 for supporting a baby.

FIG. 3 illustrates the arm sling 10 being used by a wearer 30 for holding a baby 32. The shoulder loop 16 is placed around a shoulder 34 of the wearer 30. The first and second fastenings 22 and 24 are attached so that the arm strap 18 forms an arm support loop 34 for supporting the wrist portion of the arm 36 extending from the other shoulder 38 of the wearer 30. The other arm and hand is free for other tasks. The seat of the baby 32 is supported on the arm 36 so that the baby 32 faces the wearer 30. The weight of the baby 32 is carried by the arm support loop 34 to the shoulder loop 16 and then to the shoulder 34, thereby reducing arm fatigue for the wearer 30. The first and second fastenings 22 and 24 may detached, repositioned, and reattached until the arm support loop 34 is a desired length with the free hand without removing the sling 10 or the baby 32. When not in use, the entire arm sling 10 is folded and squeezed into a compact bundle having dimensions approximately four to ten centimeters by fifteen to twenty centimeters by three and one half to four centimeters and stowed in a pants pocket or purse.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. An arm sling comprising:
    a flexible shoulder loop, including a longitudinal direction, for mounting about and being supported on a shoulder of a wearer, the shoulder loop including a pressure-sensitive first fastening strip on a forward facing side;
    a flexible arm strap extending in said longitudinal direction from the shoulder loop to a strap end section including a mating pressure-sensitive second fastening strip for fastening to said first fastening strip for forming an arm support loop having an adjustable size for supporting the arm extending from the other shoulder of said wearer.

2. The sling of claim 1, wherein:
    the shoulder loop and the arm strap are constructed of padded cloth.

3. The sling of claim 1, wherein:
    the shoulder loop has a width in a range of four centimeters to ten centimeters; and
    the arm strap has a width in a range of four centimeters to ten centimeters.

4. The sling of claim 1, wherein:
    the shoulder loop has a length in a range of sixty to one hundred centimeters.

5. The sling of claim 1, wherein:
    the shoulder loop and the arm strap are constructed of a continuous material having a length in a range of one hundred thirty to one hundred seventy centimeters.

6. The sling of claim 1, wherein:
    said arm support loop is for supporting said arm while holding a baby.

7. A method for a wearer for supporting an arm, the method comprising steps of:
    providing an arm sling having a shoulder loop having a pressure-sensitive first fastening on a forward facing side and an arm strap extending from said shoulder loop in a longitudinal direction of said shoulder loop to a strap end section having a mating pressure-sensitive second fastening;
    supporting said shoulder loop on a shoulder by placing said shoulder through said shoulder loop and resting said shoulder loop on said shoulder;
    pressing said second fastening against said first fastening for fastening said strap end section to said shoulder loop for making an arm support loop; and
    supporting the arm extending from the opposite shoulder in said arm support loop.

8. The method of claim 7, further including a step of:
    supporting a baby with said arm.

9. The method of claim 7, further including steps of:
    folding and squeezing said arm sling into a compact bundle; and
    stowing said bundle in a pants pocket.

* * * * *